United States Patent
Helbing

(10) Patent No.: US 7,280,201 B2
(45) Date of Patent: Oct. 9, 2007

(54) SENSOR HAVING INTEGRATED LIGHT DETECTOR AND/OR LIGHT SOURCE

(75) Inventor: Rene Helbing, Palo Alto, CA (US)

(73) Assignee: Avago Technologies General IP Pte Ltd, Singapore (SG)

( * ) Notice: Subject to any disclaimer, the term of this patent is extended or adjusted under 35 U.S.C. 154(b) by 302 days.

(21) Appl. No.: 11/013,373

(22) Filed: Dec. 17, 2004

(65) Prior Publication Data

US 2006/0132786 A1    Jun. 22, 2006

(51) Int. Cl.
*G01N 21/01* (2006.01)
(52) U.S. Cl. .................. 356/244; 436/172; 422/82; 422/82.07
(58) Field of Classification Search .............. 356/244; 436/172; 422/82, 82.07; 250/458.1
See application file for complete search history.

(56) References Cited

U.S. PATENT DOCUMENTS

| | | | | |
|---|---|---|---|---|
| 4,926,231 | A * | 5/1990 | Hwang et al. | 257/458 |
| 6,331,438 | B1 * | 12/2001 | Aylott et al. | 436/172 |
| 2002/0092973 | A1 | 7/2002 | Nagle et al. | |
| 2003/0156290 | A1 * | 8/2003 | Colvin et al. | 356/411 |
| 2003/0169066 | A1 * | 9/2003 | Uh et al. | 324/770 |
| 2004/0065806 | A1 | 4/2004 | Bradley et al. | |
| 2004/0086871 | A1 | 5/2004 | Schembri | |
| 2004/0241881 | A1 * | 12/2004 | Kuriger | 436/518 |

FOREIGN PATENT DOCUMENTS

WO    WO 2004/048881    6/2004

OTHER PUBLICATIONS

European Search Report for corresponding European Patent Application No. 052578000.2 dated Mar. 9, 2006.
V. Savvate'ev, et al. "Integrated Organic Light-Emitting Device/Fluorescence-Based Chemical Sensors", Applied Physics Letters, vol. 81, No. 24, Dec. 9, 2002.
Naganuma Mitsuru, "Optical Integrated Circuit", Patent Abstracts of Japan, English language Publication No. 06037300, Publication Date Feb. 10, 1994.

* cited by examiner

*Primary Examiner*—Gregory J. Toatley, Jr.
*Assistant Examiner*—Abdullahi Nur

(57) ABSTRACT

A sensor, such as a lateral flow sensor, which includes a chemical layer and a detector on a flexible substrate. An optical signal is produced in response to an analyte placed on the chemical layer. The detector detects the signal, to thereby detect the presence, absence or concentration of the analyte. The detector is on the substrate. The chemical layer and the substrate are laminated together, to thereby form an integrated sensor. The sensor can include a light source. The light source can be on the substrate, or on an opposite side of the chemical layer than the detector.

14 Claims, 7 Drawing Sheets

SENSOR HAVING INTEGRATED LIGHT DETECTOR AND/OR LIGHT SOURCE

BACKGROUND OF THE INVENTION

Description of the Related Art

There are many different types of sensors, such as biosensors and chemical sensors, that are commonly used to detect a variety of conditions and body functions. For example, biosensors and chemical sensors are commonly used for home pregnancy testing, blood sugar testing and drug testing. Some of these sensors use integrated optical detection to improve readability and accuracy.

For example, FIG. 1 is a diagram illustrating a conventional lateral flow biosensor, which is a specific type of biosensor. Referring now to FIG. 1, an analyte (i.e., a sample being tested) 10 is placed on a chemical layer 12. Chemical layer 12 is typically referred to as a "test strip" when used in a lateral flow biosensor. Analyte 10 laterally flows across chemical layer 12 to a detection zone 16 via capillary action, typically resulting, for example, in some chemical or physical modification of analyte 10, or resulting in modification of chemicals or materials in or on chemical layer 12. An optical signal 14 is produced in response to the modification. The presence, absence or the concentration of analyte 10 in zone 16 of chemical layer 12 can be determined from signal 14.

With many types of lateral flow biosensors, the modification of analyte 10 or chemicals or materials in or on chemical layer 12 causes an absorption change in zone 16, either in intensity or wavelength. Therefore, signal 14 is simply a color change that is visually identified by a person.

However, color based tests are difficult to quantify visually by a person because the degree of absorption change is difficult to judge. Therefore, if a test requires a quantitative measurement (such as, for example, in a blood sugar test), an optical detector is often provided to read signal 14.

For example, in FIG. 1, light detector 18 is provided to read signal 14. Light detector 18 detects signal 14, to thereby detect the presence, absence or concentration of analyte 10. Signal 14 is an optical signal, so that light detector 18 is conventionally a photodiode which produces an electrical output corresponding to the intensity of the detected signal 14. Light detector 18 is connected to an external display device (not illustrated) to display, for example, a numerical readout or other indication corresponding to the electrical output of light detector 18.

As indicated above, with many lateral flow biosensors, signal 14 is produced in response to an absorption change. Ambient light is sometimes sufficient for detector 18 to detect a signal 14 produced in response to an absorption change. If so, the sensor might not include a light source. However, if ambient light is not sufficient, then sensor 30 would include a light source 20, such as an LED or laser.

Moreover, some sensors require a light source to produce signal 14. For example, light source 20 might be an LED or laser which emits a light that causes fluorescence to occur, and thereby causes signal 14 to be produced.

Optical components 22 and 24, which may be optical lens and/or filters, are often provided to improve performance of the sensor.

In a conventional sensor, light source 20, light detector 18, optical components 22 and 24 are discrete, relatively large components, which are assembled and held in place by mechanical fixtures. As a result, the sensor is overly large, and can be expensive to produce.

In addition, many sensors are intended to be disposable sensors. For example, the sensor might be provided in an enclosure 25, which could be a disposable box. The use of discrete, individually assembled components for light source 20, detector 18 and optical components 22 and 24 makes the sensor prohibitively expensive as a disposable sensor.

As an example, METRICA produces such a disposable sensor for glycomic management. However, the sensor is assembled from discrete components, i.e., discrete LEDs, discrete optics, discrete photodiodes. As a result, the sensor is relatively expensive for one time use.

Therefore, in many conventional sensors, light source 20, detector 18 and optical components 22 and 24 are included in a separate, reusable, external optical system that is used with a disposable test strip or chemical layer 12. However, reusing such an external optical system has many disadvantages. For example, with home use, the user must carry around both the external optical system and test strips. For tests that are done infrequently, the user has to remember the location of the external optical system. Moreover, with a reusable external optical system, there is a danger of cross contamination between tests, especially when the optical system is used repeatedly for multiple tests such as in a doctor's office. The chance of cross contamination is especially troublesome in drug testing, where even the remote possibility of cross transfer can result in legal challenges of the outcome of the test.

SUMMARY OF THE INVENTION

Various embodiments of the present invention provide an apparatus including (a) a chemical layer via which an optical signal is produced in response to an analyte being placed on the chemical layer; (b) a detector which detects the optical signal to thereby detect presence, absence or concentration of the analyte; and (c) a substrate, wherein the detector is on the substrate, and the chemical layer and the substrate are laminated together.

Moreover, various embodiments of the present invention provide an apparatus including (a) a chemical layer via which an optical signal is produced in response to an analyte being placed on the chemical layer; (b) a detector, being an organic photodiode or amorphous silicon, which detects the signal to thereby detect the presence, absence or concentration of the analyte; (c) an organic light emitting diode (OLED) which emits a light that causes the optical signal to be produced or detected in response to the analyte being placed on the chemical layer; and (d) a substrate, wherein the detector and the OLED are manufactured directly on the substrate, and the chemical layer and the substrate are laminated together.

In addition, various embodiments of the present invention provide an apparatus including (a) a chemical layer via which an optical signal is produced in response to an analyte being placed on the chemical layer; and (b) a detector which detects the signal, to thereby detect presence, absence or concentration of the analyte, wherein the chemical layer and the detector are integrated together by lamination.

BRIEF DESCRIPTION OF THE DRAWINGS

These and other aspects and advantages of the invention will become apparent and more readily appreciated from the following description of the preferred embodiments, taken in conjunction with the accompanying drawings of which.

DESCRIPTION OF THE PREFERRED EMBODIMENTS

Figure 1:
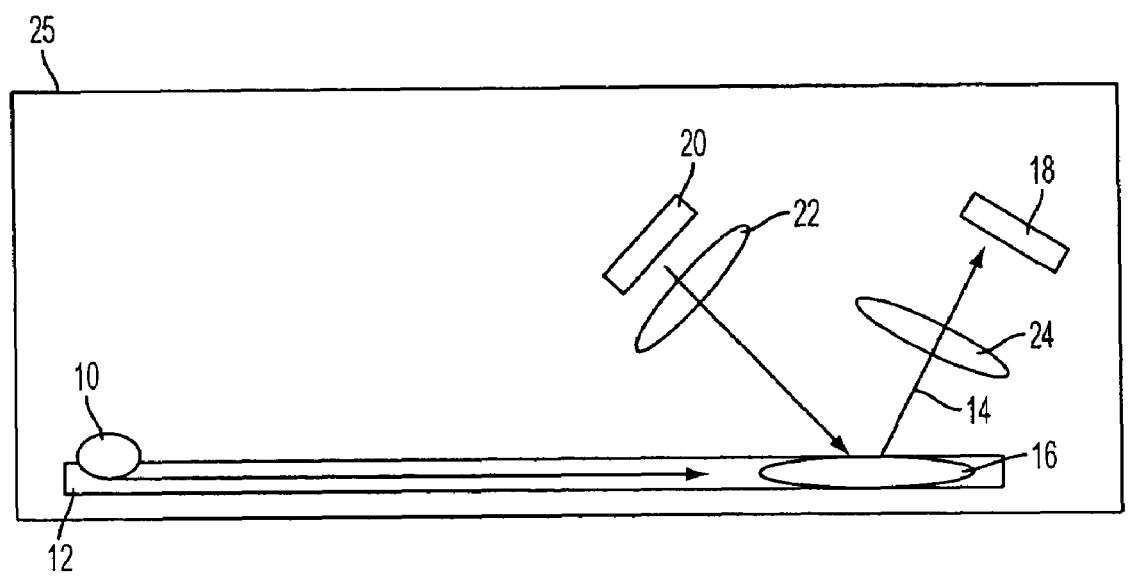
FIG. 1 (prior art) is a diagram illustrating a conventional lateral flow biosensor.

Reference will now be made in detail to the present preferred embodiments of the present invention, examples of which are illustrated in the accompanying drawings, wherein like reference numerals refer to like elements throughout.

Figure 2:
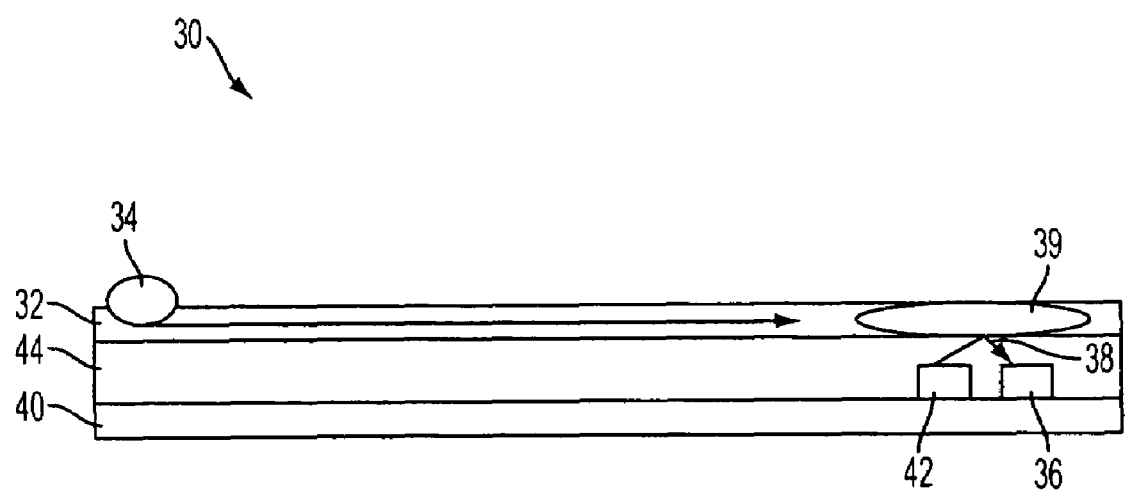
FIG. 2 is a diagram illustrating a sensor according to an embodiment of the present invention.

FIG. 2 is a diagram illustrating a sensor 30 according to an embodiment of the present invention. In FIG. 2, sensor 30 is a lateral flow biosensor. However, the present invention is not limited to being a "lateral flow" biosensor. Instead, the present invention is applicable to biosensors other than "lateral flow" biosensors. Moreover, the present invention is not limited to being a "biosensor". Instead, the present invention is applicable to many different types of sensors, including biosensors and chemical sensors.

Referring now to FIG. 2, sensor 30 includes a chemical layer 32. When an analyte 34 is placed on chemical layer 32, an optical signal 38 is produced in zone 39 of chemical layer 32. For example, optical signal 38 is produced in response to a chemical or physical modification of analyte 34, or a chemical or physical modification of a chemical or material in or on chemical layer 32. A detector 36 detects signal 38, to thereby detect the presence, absence or concentration of analyte 34. For example, in some embodiments, the presence of analyte 34 would be detected. In other embodiments, the concentration of analyte 34 would be detected. Detector 36 is placed in appropriate proximity to zone 39 to allow sufficient detection of signal 38. Detector 36 is, for example, a photodiode. However, the present invention is not limited to detector 36 being a photodiode, and other suitable detectors can be used.

In some types of sensors, it is not required for the sensor to include a light source. For example, in some sensors, detector 36 may detect an absorption change in zone 39. Ambient light might be sufficient for detector 36 to detect the change. If ambient light is sufficient, it may not necessary for the sensor to include a light source. Otherwise, a light source might be provided.

However, some sensors must include a light source. For example, some sensors require a light source to produce signal 38. As an example, a light source might be required to cause signal 38 to be produced via fluorescence.

If a light source is required to produce or detect signal 38, sensor 30 would include a light source 42. Light source 42 is, for example, a light emitting diode (LED). LEDs are well known. However, light source 42 is not limited to being an LED, and other suitable types of light sources can be used.

Sensor 30 also includes a substrate 40. Substrate 40 includes conductive elements (not illustrated) to connect components together on substrate 40 or, if necessary, to connect external components to components on substrate 40. Substrate 40 is, for example, a flexible substrate such as, for example, a polyimide substrate. Such substrates are well known. However, substrate 40 is not limited to being a flexible substrate, and is also not limited to being a polyimide substrate. Instead, other suitable substrates can be used.

Detector 36 is on substrate 40. In the embodiment in FIG. 2, if sensor 30 also includes light source 42, then light source 42 is also on substrate 40. For example, detector 36 and light source 42 are bonded to substrate 40, or attached to substrate in any suitable other manner. Chemical layer 32 and substrate 40 are laminated together. In other embodiments of the present invention, detector 36 and light source 42 can be on opposite sides of chemical layer 32. Hence, two optical layers (i.e., one layer including detector 36 and one layer including light source 42) are bonded to a chemical layer.

A separation layer 44 can be used to provide the necessary optical separation between chemical layer 32 and the optical components such as light source 42 and detector 36, which is especially important when both light source 42 and detector 36 are mounted on the same side of chemical layer 32. For example, separation layer 44 can be provided between chemical layer 32 and substrate 40 so that separation layer 44 is between chemical layer 32 and detector 36, and between chemical layer 32 and light source 42. Separation layer 44 can be, for example, a separate piece of plastic or a clear, conformal coating on top of substrate 40. Here, "clear" indicates that separate layer 44 is "clear" to signal 38, and not necessarily "clear" to the human eye. For example, if light source 42 emits infrared light, separation layer 44 might be black in color to the human eye. Chemical layer 32, separation layer 44 and substrate 40 are laminated together.

By using an appropriate detector 36 (such as, for example, an surface mount photodiode), a suitable light source (such as, for example, an surface mount LED), and a suitable substrate (such as, for example, a polyimide flex substrate), the present invention integrates chemical layer 32, detector 36 and light source 42 together into one unit, and can be used, for example, as a disposable sensor. Such a disposable sensor would be relatively inexpensive compared to a conventional sensor. Further, such a disposable sensor would have substantial cost and size savings due to the lack of required submounts and alignments as compared to a conventional sensor. In addition, due to the proximity of detector 38 to chemical layer 32, a disposable sensor according to various embodiments of the present invention might not require any collection optics.

The integration of light source 42 and detector 36 on substrate 40 is based, for example, on flex technology. Generally, flex technology is typically used to integrate electronic components onto a flexible substrate. Flex technology is known, and has been applied for low cost manufacturing of a variety of electronic components such as, for example, CMOS cameras. For example, within conventional flex technology, the camera IC and any required passive components are directly mounted onto a flex substrate that is used to connect the camera to a PC board.

Figure 3:
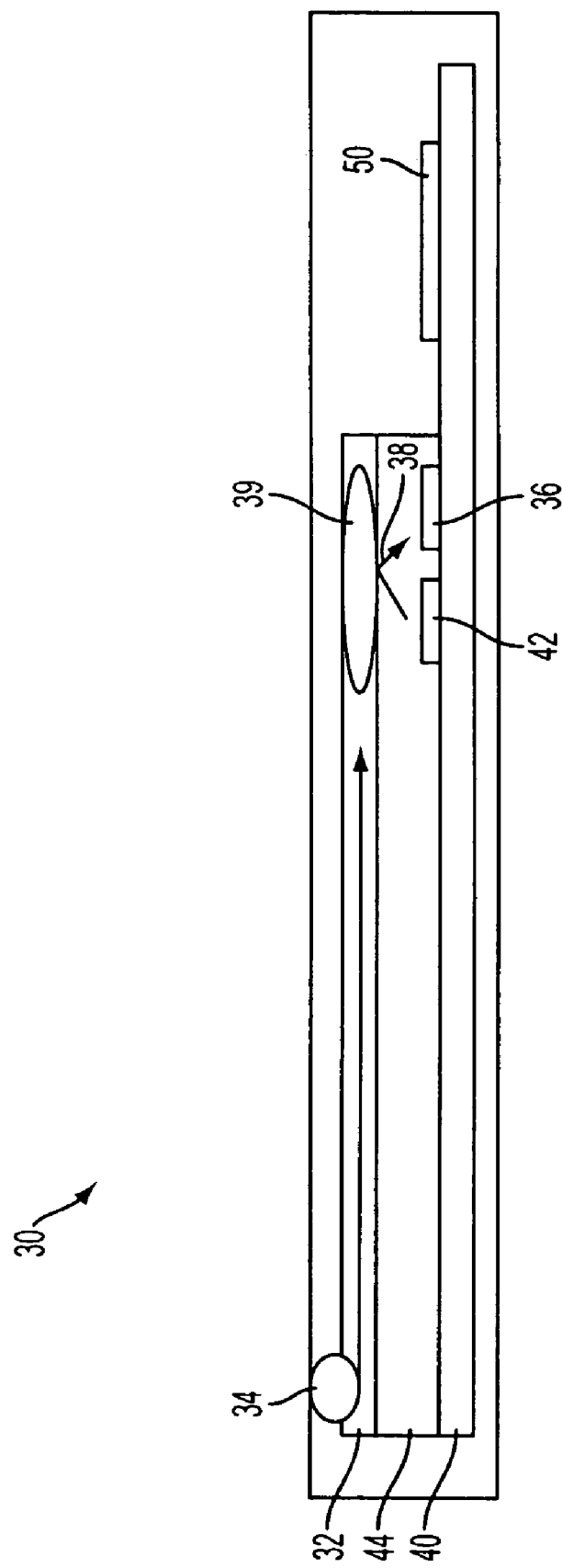
FIG. 3 is a diagram illustrating a sensor having an integrated display device, according to an embodiment of the present invention.

FIG. 3 is a diagram illustrating sensor 30 having an integrated display device, according to an embodiment of the present invention. Referring now to FIG. 3, a display device 50 is on substrate 40. For example, display device 50 is bonded to substrate 40, or attached to substrate in any suitable other manner. Display device 50 displays a result corresponding to signal 38 detected by detector 36. Display device 50 might, for example, simply provide a light which goes ON or OFF to indicate YES or NO. Or, display device 50 might, for example, provide a numerical readout corresponding, for example, to the concentration of the analyte.

Display device 50 is, for example, a light emitting diode (LED), an organic light emitting diode (OLED) or a liquid crystal display. However, display device 50 is not limited to being an LED, an OLED or a liquid crystal display, and any suitable display device can be used.

By using an appropriate display device 50 (such as, for example, an LED or a liquid crystal display), the present invention integrates chemical layer 32, detector 36, light source 42 and display device 50 together into one laminated unit, and can be used, for example, as a disposable sensor. Such a disposable sensor would be relatively inexpensive compared to a convention sensor using discrete components and a separate, external display device.

Although not shown in FIGS. 2 and 3, appropriate components such as polarizers, optical filters and other measurement supporting components, can be integrated into the optical sensor to cooperate with light source 42 and/or detector 36, if desired. These components can be, for example, bonded to substrate 40, or provided as a layer between chemical layer 32 and substrate 40, and laminated together with chemical layer 32 and substrate 40. The selection of appropriate materials for such components would be within the skill of a person of ordinary skill in the art, in view of the disclosure herein.

According to embodiments of the present invention, if the appropriate materials are selected for use as light source 42, detector 36 and substrate 40, then light source 42 and detector 36 can be manufactured directly on substrate 40. For example, light source 42 and detector 36 can be made of organic materials (such as light source 42 being an OLED and detector 36 being an organic photodiode). Alternatively, detector 36 can be of a material such as, for example, amorphous silicon. In addition, substrate 40 can be, for example, a flexible substrate such as, for example, a polyimide substrate. With such material selection, light source 42 and detector 36 can be manufactured directly on substrate 40. As a result, the sensor can be manufactured by a potentially low cost manufacturing method. The manufacturing of a light source such, for example, as an OLED on a substrate, such as, for example, a flexible substrate, is known. The manufacturing of a detector such as, for example, an organic photodiode or amorphous silicon, directly on a substrate, such as, for example, a flexible substrate, is known.

Although not shown in FIG. 2 or 3, a power source would also typically be provided on the sensor. A power supply for integration in such a sensor would be understood by a person of ordinary skill in the art in view of this disclosure.

Moreover, although not shown in FIG. 3, a processing device might be provided on substrate 40 to process the output signal of detector 36 for use by display device 50. A processing device in such a sensor would be understood by a person of ordinary skill in the art in view of this disclosure.

Sensor 30 in FIGS. 2 and 3 is a lateral flow biosensor, since analyte 34 laterally flows across chemical layer 32, which causes signal 38 to be produced in zone 39. However, the present invention also applies to sensors which are not lateral flow biosensors.

Figure 4:
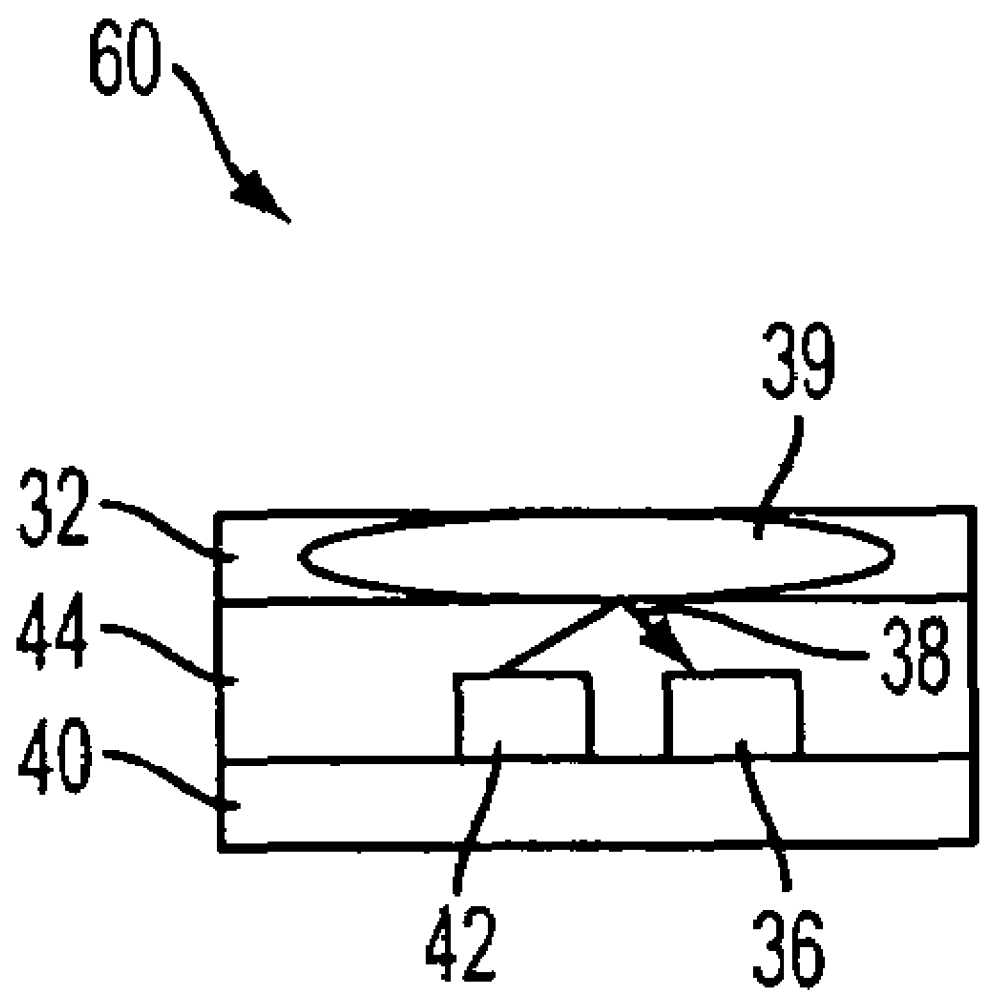
FIGS. 4 and 5 are diagrams illustrating a sensor according to an additional embodiment of the present invention.
Figure 5:
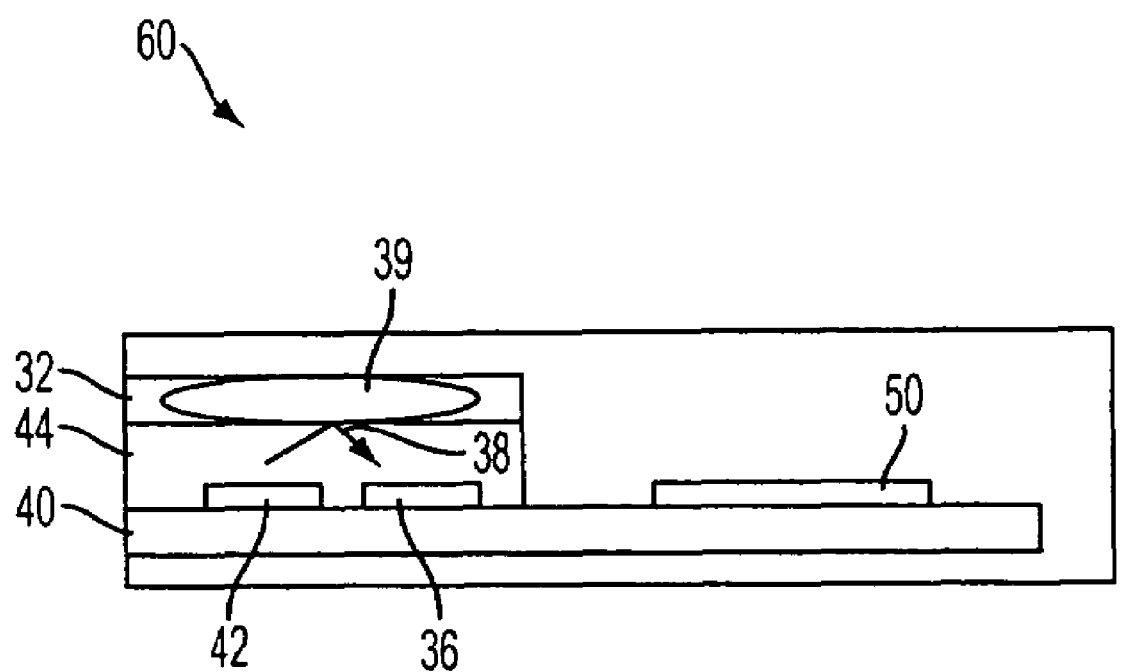

For example, FIGS. 4 and 5 illustrate a sensor 60 according to additional embodiments of the present invention. Sensor 60 is not a lateral flow sensor. Referring now to FIGS. 4 and 5, an analyte (not illustrated in FIGS. 4 and 5) is placed directly in zone 39, to thereby produce signal 38. Otherwise, sensor 60 in FIGS. 4 and 5 is similar to sensor 30 in FIGS. 2 and 3, respectively.

In FIGS. 2-5, light source 42 and detector 36 are on the same side of chemical layer 32 with respect to each other. However, in some embodiments, light source 42 and detector 36 can be on opposite sides of chemical layer 32 with respect to each other.

Figure 6:
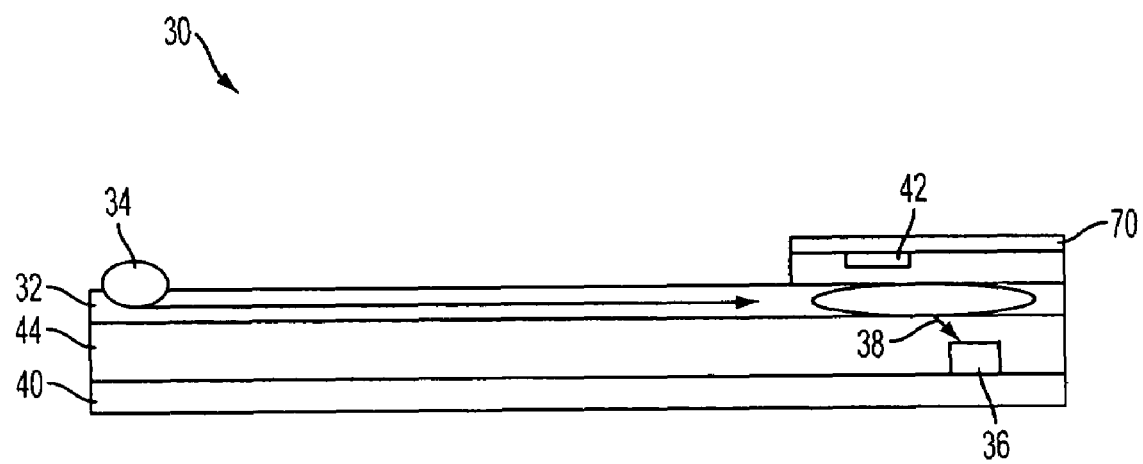
FIGS. 6 and 7 illustrate a sensor having a light source and detector on opposite sides of a chemical layer, according to an embodiment of the present invention.
Figure 7:
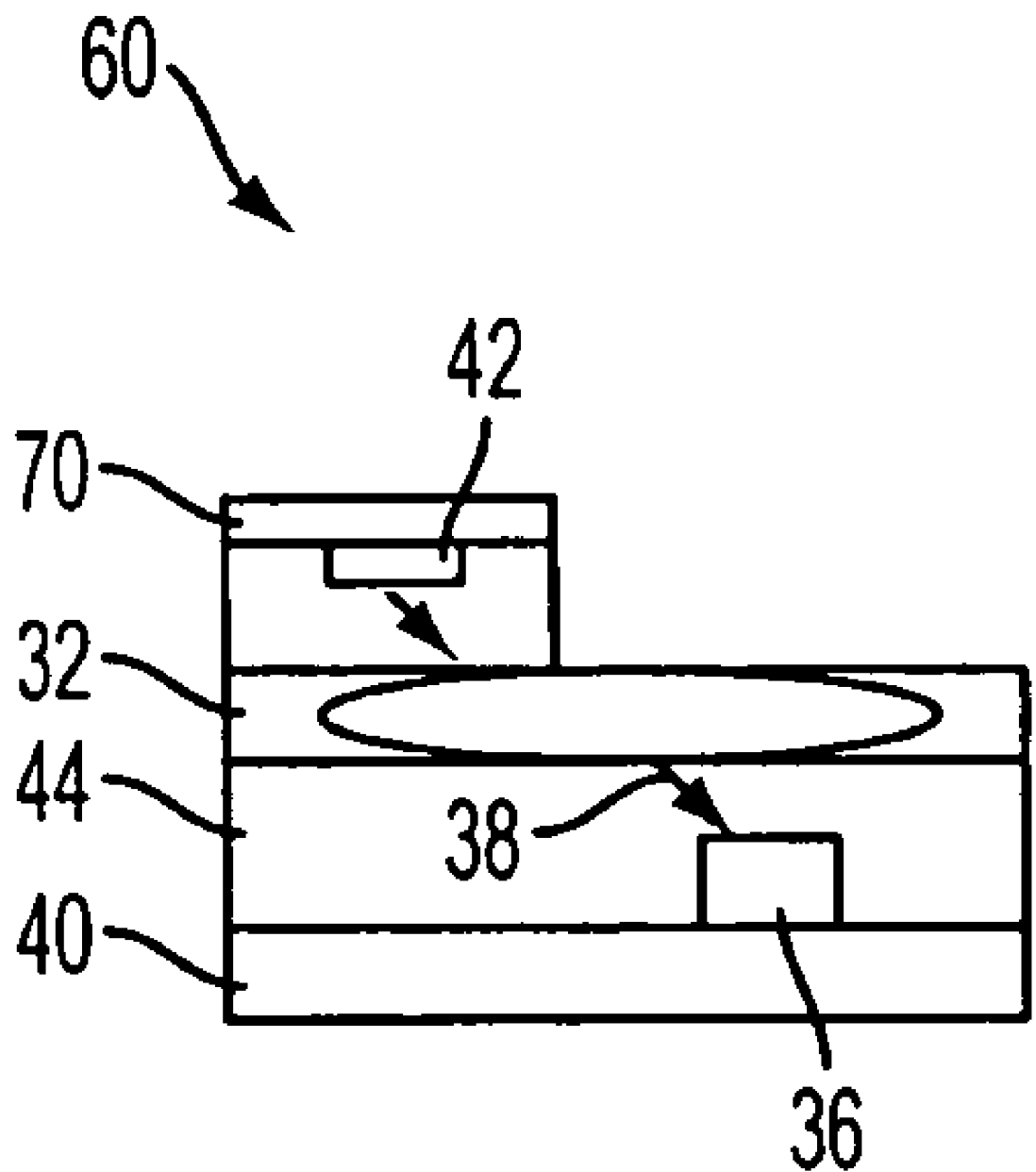

For example, FIGS. 6 and 7 illustrate a sensor having a light source and detector on opposite sides of chemical layer 32. Referring now to FIGS. 6 and 7, light source 42 is provided on a separate substrate 70. Substrate 70 might be, for example, a flexible substrate such as, for example, a polyimide substrate. However, substrate 70 is not limited to being a flexible substrate or a polyimide substrate. Chemical layer 32 is sandwiched between substrates 40 and 70. Although separation layer 44 is shown in FIGS. 6 and 7, a separation layer would often not be necessary, and could be eliminated, if light source 42 and detector 36 are on opposite sides of chemical layer 32. Further, a display device, such as display device 50 in FIGS. 3 and 5, could be positioned on either substrate 40 or 70.

In FIGS. 6 and 7, substrate 70 is shown as being much shorter in length than substrate 40. The present invention is not limited to substrate 70 being any specific length or size with respect to substrate 40. In some embodiments of the present invention, a window (not illustrated) could be provided on substrate 70 to allow an analyte to be passed through the window and be placed on chemical layer 32.

There are many different types of sensors that operate in different manners. The present invention is not limited to any particular type of sensor. The present invention is particularly applicable to biosensors and chemical sensors. Moreover, there are many different types of chemical layers or test strips that can be used in a sensor, and these chemical layers or test strips can operate with different underlying chemicals and in accordance with different mechanisms of action. The present invention is not limited to any particular type of chemical layer or test strip, to any particular underlying chemical, or to any particular mechanism of action.

Although a few preferred embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An apparatus comprising:
    a chemical layer via which an optical signal is produced in response to an analyte being placed on the chemical layer;
    a detector which detects the optical signal to thereby detect presence, absence, or concentration of the analyte;
    a substrate, wherein the detector is on the substrate; and
    a separation layer between the chemical layer and the substrate and over the detector, wherein:
        the separation layer is transparent to the optical signal;
        the chemical layer, the separation layer, and the substrate are laminated together, and
        the separation layer providing optical separation between the chemical layer and the detector.

2. An apparatus as in claim 1, further comprising:
    a light source which emits a light that causes the optical signal to be produced or detected in response to the analyte being placed on the chemical layer, wherein the light source is on the substrate and laterally displaced from the detector.

3. An apparatus as in claim 1, wherein said substrate is a first substrate and said separation layer is a first separation layer, the apparatus further comprising:
a second substrate; and
a light source which emits a light that causes the signal to be produced or detected in response to the analyte being placed on the chemical layer;
a second separation layer between the chemical layer and the second substrate and covering the light source, wherein
the light source is on the second substrate,
the chemical layer is sandwiched between the first and the second substrates, and
the first substrate, the first separation layer, the chemical layer, the second separation layer, and the second substrate are laminated together.

4. An apparatus as in claim 1, wherein the apparatus is a lateral flow sensor and the chemical layer is a test strip for the lateral flow sensor.

5. An apparatus as in claim 1, wherein the substrate is a flexible substrate.

6. An apparatus as in claim 1, wherein the detector is a photodiode.

7. An apparatus as in claim 2, wherein the light source is a light emitting diode (LED).

8. An apparatus as in claim 1, further comprising:
a display device on the substrate and which displays a result corresponding to the signal detected by the detector.

9. An apparatus as in claim 8, wherein the display device is a light emitting diode (LED) or a liquid crystal display (LCD).

10. An apparatus as in claim 2, further comprising:
a display device on the substrate and which displays a result corresponding to the signal detected by the detector.

11. An apparatus as in claim 10, wherein the display device is a light emitting diode (LED) or a liquid crystal display (LCD).

12. An apparatus comprising:
a chemical layer via which an optical signal is produced in response to an analyte being placed on the chemical layer;
a detector, being an organic photodiode or amorphous silicon, which detects the signal to thereby detect the presence, absence or concentration of the analyte;
an organic light emitting diode (OLED) which emits a light that causes the optical signal to be produced or detected in response to the analyte being placed on the chemical layer; and
a substrate, wherein the detector and the OLED are manufactured directly on the substrate, and the chemical layer and the substrate are laminated together.

13. An apparatus as in claim 12, further comprising:
a display device on the substrate and which displays a result corresponding to the signal detected by the detector.

14. An apparatus as in claim 13, wherein the display device is an organic light emitting diode (OLED) or a polymer stabilized liquid crystal display which is manufactured directly on the substrate.

* * * * *